United States Patent [19]

Dawson et al.

[11] Patent Number: 5,643,327
[45] Date of Patent: Jul. 1, 1997

[54] PACEMAKER AND METHOD HAVING OPTIMIZED A-V DELAY BY USING THE EVOKED DEPOLARIZATION POTENTIAL AS AN INDICIA OF CARDIAC OUTPUT

[75] Inventors: Albert K. Dawson, Littleton; Tibor Nappholz, Englewood, both of Colo.

[73] Assignee: Pacesetter, Inc., Sylmar, Calif.

[21] Appl. No.: 492,479

[22] Filed: Jun. 20, 1995

[51] Int. Cl.$^6$ ................................................. A61N 1/365
[52] U.S. Cl. ......................................................... 607/24
[58] Field of Search ................................ 607/9, 14, 17, 607/24, 25

[56] References Cited

U.S. PATENT DOCUMENTS

| | | | |
|---|---|---|---|
| 4,303,075 | 12/1981 | Heilman et al. | 128/419 PC |
| 4,702,253 | 10/1987 | Nappholz et al. | 128/419 PG |
| 4,766,901 | 8/1988 | Callaghan | 128/419 PG |
| 4,901,725 | 2/1990 | Nappholz et al. | 128/419 PG |
| 5,184,615 | 2/1993 | Nappholz et al. | 128/419 PG |
| 5,201,808 | 4/1993 | Steinhaus et al. | 128/419 PG |
| 5,292,340 | 3/1994 | Crosby et al. | 607/17 |
| 5,330,511 | 7/1994 | Boute | 607/25 |
| 5,334,222 | 8/1994 | Salo et al. | 607/24 |
| 5,480,413 | 1/1996 | Greenhut et al. | 607/14 |

OTHER PUBLICATIONS

NASPE Abstracts, Pace, vol. 16, Apr. 1993, Part II.
The Information Content of the Cardiac Electrogram at the Stimulus Site, Bruce M. Steinhaus and Tibor A. Nappholz, Annual International Conference of the IEEE Engineering in Medicine and Biology Society,, vol. 12, No. 2, 1990, pp. 0607–0609.

*Primary Examiner*—William E. Kamm
*Attorney, Agent, or Firm*—Gottlieb, Rackman & Reisman

[57] ABSTRACT

The cardiac output of a paced heart is optimized by measuring a parameter indicative of the volume of blood in a heart chamber as a function of a pacing parameter. The pacing parameter is adjusted so that the heart pumps the maximum volume at different rates for hearts with debilitating pathologies. This pacing parameter is then used for controlling the pacing pulses for pacing the heart. Preferably the volume parameter is the paced depolarization integral and the pacing parameter is the A-V delay.

17 Claims, 9 Drawing Sheets

PACEMAKER AND METHOD HAVING OPTIMIZED A-V DELAY BY USING THE EVOKED DEPOLARIZATION POTENTIAL AS AN INDICIA OF CARDIAC OUTPUT

BACKGROUND OF THE INVENTION

A. Field of Invention

This invention pertains to a pacemaker that automatically monitors the capability of an impaired heart to increase cardiac output with increased rate and to optimize the AV delay in such a way that the ability to increase cardiac output with rate is maximized. To enable this function to be carried out, it is suggested to use the integral of the evoked electrical depolarization as an indicator of the change in the cardiac volume that leads to a modulation of cardiac output.

B. Description of the Prior Art

The primary function of a dual chamber pacemaker is to monitor the occurrence of atrial events (P waves) and on the detection of these events, to set up an atrio-ventricular delay (AV delay). The ventricle is paced at the end of this delay unless a ventricular event is sensed. If atrial events are not sensed within a specified time period (standby interval) an atrial pacing pulse is generated and subsequent: ventricular pacing pulse is applied after the specified AV delay. It is common to have an AV delay after a P wave which differs from an AV delay after an A pace. The reason for this feature is that the atrial electrode is positioned away from the direct path of the depolarization traveling from the sinus node to the ventricle. In general, the AV delay after an A sense is shorter than that after an A pace.

The actual cardiac output, in particular at rest, is often influenced by the AV delay. This implies that optimum function of the heart is achieved with optimum AV delay which is different for each patient. Prior art references such as U.S. Pat. No. 4,303,075 and 5,330,511 discuss the automatic adjustment of the AV delay based on certain hemodynamic or metabolic indicators. All these known concepts assume that the optimization of the AV delay at a particular rate allows correct optimization for all rates and they do not take into consideration the possibility that at different rates (in particular higher rates) the AV delay has to be dramatically changed because of underlying pathologies that are not present in normal hearts. The mechanisms that come into play with impaired hearts that need particular attention are the regurgitation of valves, in particular the mitral valve, and the change in the ability of the ventricle to pump at higher rates because of the additional stress to an already overloaded heart. These factors imply that what is needed is to establish that the increase in rate that is demanded of the heart can in fact increase cardiac output with an optimized AV delay.

The invention is preferably implemented in dual chamber pacemakers in combination with other features such as rate response, maximum rate controls, AMS and so on.

OBJECTIVES AND SUMMARY OF THE INVENTION

It is an objective of the present invention to provide a pacemaker in which a volume parameter is determined to allow the adjustment of the AV delay in a manner so as to keep the myocardial contraction process in an optimum region in order to minimize unnecessary stress on the heart particularly in the presence of valvular regurgitation and heart failure.

A further objective of this invention is developing a pacemaker which takes into consideration the capability of the heart to respond to a metabolic demand and that an impaired heart has physiological limitations which, if ignored lead to long term damage to the heart and, very often, premature mortality.

The heart operates like a pump which over short periods can be seen as having to establish a certain flow rate. This flow rate is the product of each stroke volume and the heart rate. If there is increased mitral regurgitation, or if ventricular contractility is inadequate, abnormal patterns in ventricular distention can be observed. This change in distention is measured by the ventricular paced depolarization integral and can be used to establish that the heart is achieving increased flow rate with an increase in heart rate, and is not operating marginally.

A serious condition is indicated when increased distention occurs with increased rate, signalling decrease in the heart contractility at higher rates. An important advantage of using the paced depolarization integral is that this parameter is a very fast indicator of hemodynamic status of the heart and hence allows rapid adjustments even during changes in metabolic demand.

Studies have shown that the paced depolarization integral (PDI) is a parameter which provides important information about certain cardiac functions. This parameter is obtained, by applying a pacing pulse to the ventricle and integrating a portion of the evoked cardiac electrogram. It has been experimentally determined that the PDI parameter is proportional to a number of physiological characteristics. (See Steinhaus and Nappholz, THE INFORMATION CONTENT OF THE CARDIAC ELECTROGRAM AT THE STIMULUS SITE, Proceedings of the Twelfth Annual International Conference of the I.E.E.E. Engineering Medicine and Biology Society, Vol.12, No.2, 1990, pp. 0607–0609.) However, during the relatively short time period of the A-V delay, the only one of the physiological characteristic controlling PDI which changes is the cross-sectional area of the myocar-dial wall, which in turn is related to the thickness of said wall. At the beginning of a cycle, i.e., when the ventricle is at its lowest volume, the myocardial wall is relatively thick, and therefore its cross sectional area is larger. As the ventricle is filled up with blood, the ventricle expands and the thickness the myocardial wall decreases. Thus, the thickness of the myocardial wall, and its cross-sectional are is related to the volume of blood in the ventricular chamber. Of course, these dimensions are very hard to measure directly in vivo, as the heart is beating. However, as described below, the PDI parameter can be determined relatively easily. Since, as discussed above, the PDI parameter is proportional to the cross-sectional area of the myocardial wall, and since the cross-sectional area of the wall is directly related to the volume of blood in the ventricle, the PDI parameter may also be used as a volume parameter for indicating the volume of blood in the ventricle.

The PDI parameter is inversely related to the ventricular blood volume. As this volume increases, the myocardial wall thickness, its cross-sectional area and therefore the PDI parameter, all decrease. Hence, ventricular filling is maximized when the PDI parameter is at a minimum value. Thus, in ventricles with normal contractility, a minimum PDI indicates a maximal stroke volume and so a maximal cardiac output for a given heart rate.

The present invention takes advantage of this phenomenon by adjusting the A-V delay within the pacemaker to conform to the optimized volume parameter, i.e., minimum acceptable PDI value. This delay then automatically results in a maximized cardiac output.

Preferably, a curve characteristic of the relationship between the volume parameter and the pacing parameter is obtained by pacing the heart of a patient within a preselected range of A-V delays, and for each pacing parameter obtaining a corresponding volume parameter. The volume parameter corresponding to the optimized cardiac output is used to select the pacing parameter.

DETAILED DESCRIPTION OF THE INVENTION

A pacemaker incorporating the present invention is shown in FIGS. 1–4. Except for the features covering the adjusting of the A-V delay in accordance with the PDI parameter to optimize cardiac output, the pacemaker of these Figures is constructed and operates in accordance with the description found in commonly assigned copending application SN 226,654, filed Apr.12, 1994 by Tibor A. Nappholz, entitled FORCED ATRIOVENTRICULAR SYNCHRONY DUAL CHAMBER PACEMAKER, now U.S. Pat. No. 5,441,523, incorporated herein by reference.

Figure 1:
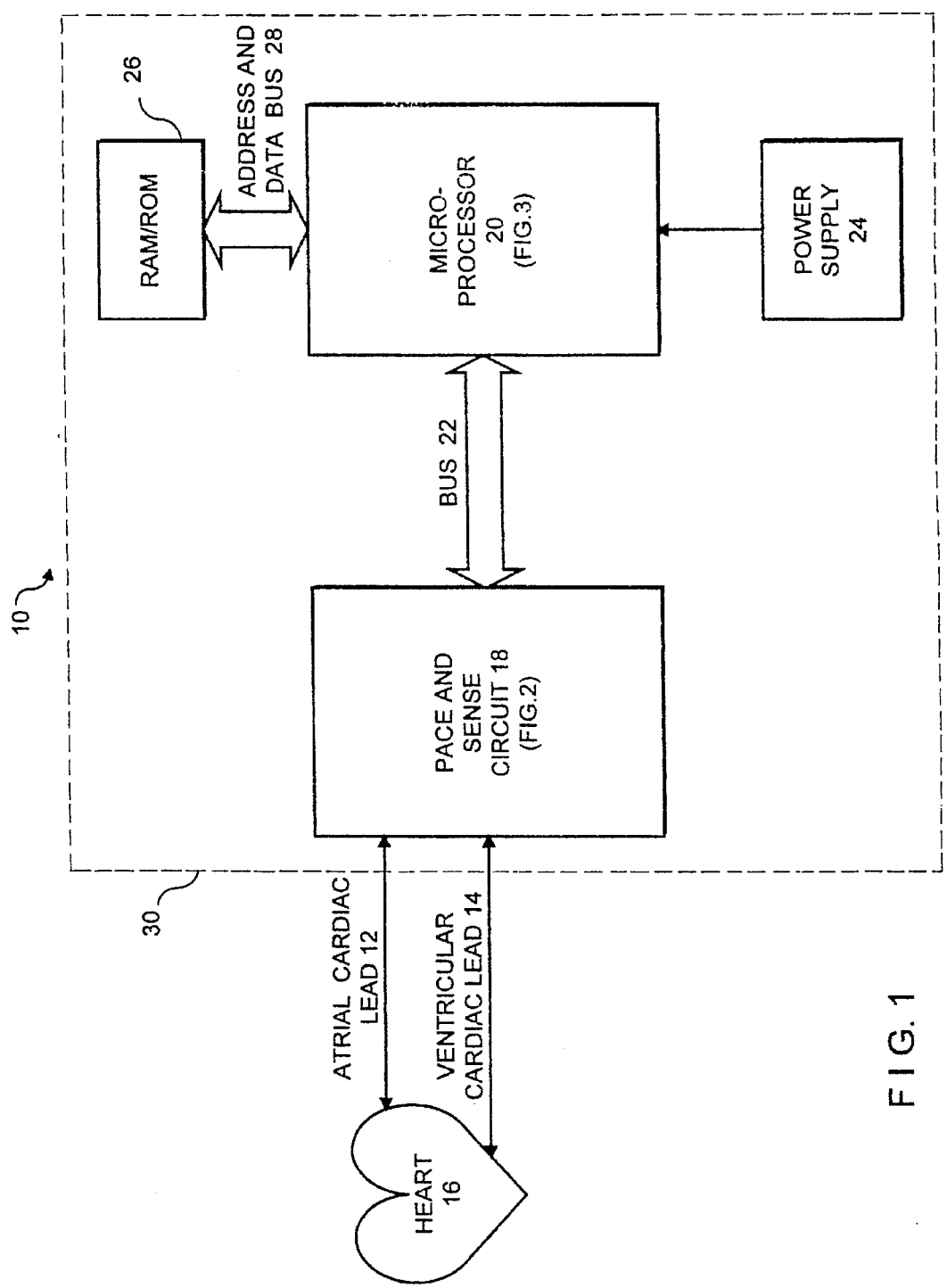
FIG. 1 shows a block diagram of a pacemaker constructed in accordance with this invention.

Briefly, the pacemaker 10 shown in FIG. 1 is designed to be implanted in a patient and is connected by leads 12 and 14 to a patient's heart 16 for sensing and pacing the same. The atrial cardiac lead 12 extends into the atrium of the heart 16 and the ventricular cardiac lead 14 extends into the ventricle of the heart 16 and incorporated herein by reference. Leads 12 and 14 are used for both sensing electrical activity in the heart and for applying pacing pulses to the heart. The pacemaker 10 includes a pace and sense circuit 18 for the detection of analog signals from leads 12 and 14 and for the delivery of pacing pulses to the heart; a microprocessor 20 which, in response to inputs received from the pace and sense circuit 18, performs operations to generate different control and data outputs to the pace and sense circuit 18; and a power supply 24 which provides a voltage supply to the pace and sense circuit 18 and the microprocessor 20. The microprocessor 20 is connected to a random access memory/read only memory unit 26 by an address and data bus 28, all powered by power supply 24. The microprocessor 20 and the pace and sense circuit 18 are connected to each other by a number of data and control lines included in bus 22.

Figure 2:
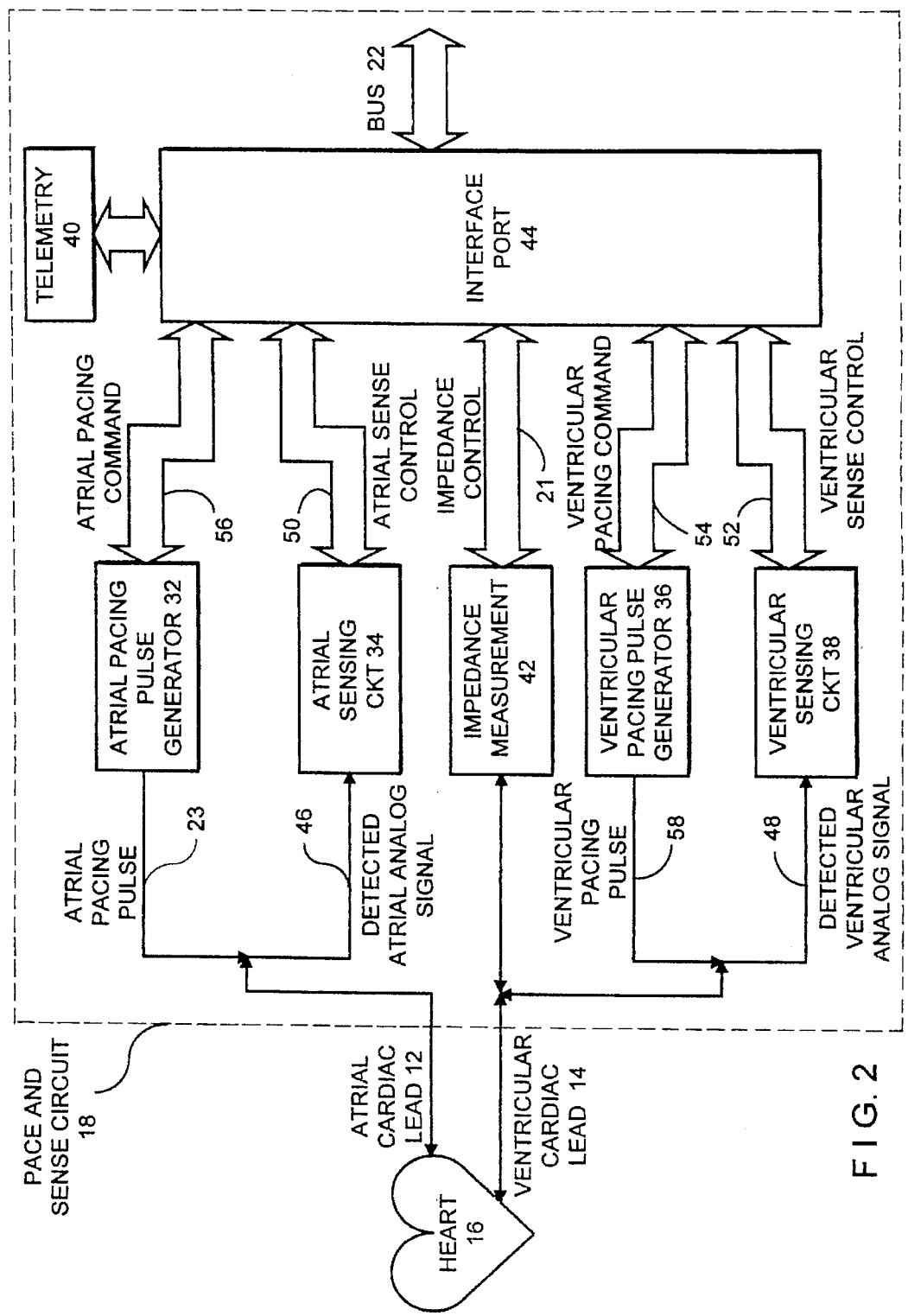
FIG. 2 shows a block diagram showing details of the pace and sense circuit for the pacemaker of FIG. 1.

FIG. 2 shows details of the pace and sense circuit 18. The circuit 18 includes an atrial pacing pulse generator 32, a ventricular charge balanced pacing pulse generator 36, an atrial heartbeat sensor 34, a ventricular sensor 38, and a telemetry circuit 40. A generator for cardiac charge balanced stimulation, to enable evoked potential measurement, is discussed in commonly assigned U.S. Pat. No. 5,178,140. The preferred embodiment of the pace and sense circuit 18 also includes an impedance measurement circuit 42 for measuring a respiratory parameter indicative of the patient's metabolic demand as described in detail in U.S. Pat. No. 4,901,725 and incorporated herein by reference. The pace and sense circuit 18 also includes an interface port 44 for interfacing with the microprocessor 20 via bus 22.

In operation, the atrial and ventricular sensing circuits 34 and 38 detect respective atrial and ventricular analog signals 46 and 48 from the heart 16 and convert the detected analog signals to digital signals.

The atrial pacing pulse generator circuit 32 receives via microprocessor 20 and interface port 44 on bus 56, an atrial pace command to generate an atrial pacing pulse 23 at appropriate times. Similarly, the ventricular pacing pulse generator circuit 36 receives from the interface port 44, and control bus 54, a ventricular pace command to generate a ventricular pacing pulse 58.

The telemetry circuit 40 provides a bidirectional link between the interface port 44 of the pace and sense circuit 18 and an external device such as a programmer. It allows data such as the operating parameters to be read from or altered in the implanted pacemaker. An exemplary programmer is the 9600 Network Programmer manufactured by Telectronics Pacing Systems, Inc. of Englewood, Colo., U.S.A.

Figure 3:
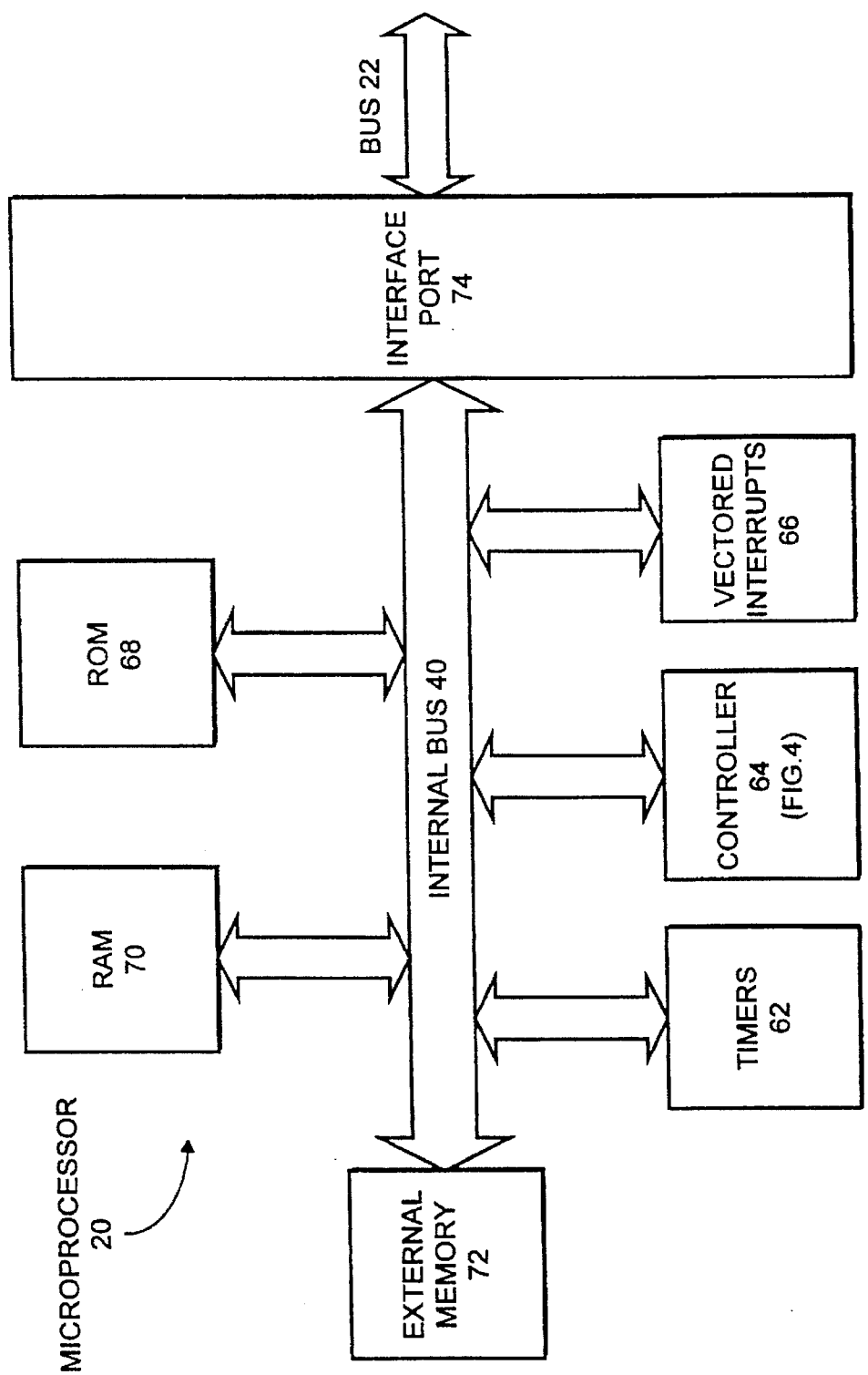
FIG. 3 shows details of the microprocessor for the pacemaker of FIG. 1.

FIG. 3 shows the microprocessor 20 having a timer circuit 62 for generating several timing signals on its output ports A–E, a controller 64, a vectored interrupts circuit 66, a ROM 68, a RAM 70, an external memory 72 and an interface port 74. Signals between these elements are exchanged via an internal communications bus 40. Timer circuits generate various timing signals at its output ports A–E. The RAM 70 acts as a scratchpad and active memory during execution of the programs stored in the ROM 68 and used by the microprocessor 20. ROM 68 is used to store various subroutines.

The microprocessor 20 through its interface port 74 receives status inputs from the pace and sense circuit 18. Using controller 64, it performs various operations, including arrhythmia detection, and produces commands, such as the atrial pace command on the bus 56 and the ventricular pace command on the bus 54, which determine the type of pacing that is to take place as described in the previously referenced application SN 226,654 now U.S. Pat. No. 5,441,523.

The pacemaker 10 of the present invention will function properly using any metabolic indicator rate system, so long as that system is able to reliably relate the sensed parameter to a metabolic demand pacing rate. For example, U.S. Pat. No. 4,766,901, to F. Callaghan, issued Aug. 30, 1988, for "Rate Responsive Pacing System Using the Integrated Evoked Potential," refers to the operation of a rate-responsive pacing system using an integrated evoked ventricle depolarization potential (or PDI) as a metabolic demand pacing rate indicator. U.S. Pat. No. 4,702,253 to T. A. Nappholz et al., issued Oct.27, 1987, for "Metabolic-Demand Pacemaker and Method of Using the Same to Determine Minute Volume," U.S. Pat. No. 4,901,725, to T. A. Nappholz et al., issued Feb. 20, 1990 for "Minute Volume Rate-Responsive Pacemaker", and U.S. Pat. No. 5,201,808 to B. M. Steinhaus et al., entitled "Minute Volume Rate-Responsive Pacemaker Employing Impedance Sensing on a Unipolar Lead", which issued on Apr. 13, 1993, disclose rate-responsive pacers describing another metabolic demand pacing rate indicator, respiratory minute volume, as the rate control parameter. The pacemaker 10 can employ any rate response techniques available or no rate response at all. The preferred embodiment of the invention employs the impedance measurement circuit 42 which measures the cardiac and thoracic impedance to determine the respiratory minute volume in accordance with the '725 Nappholz patent mentioned above.

Figure 4:
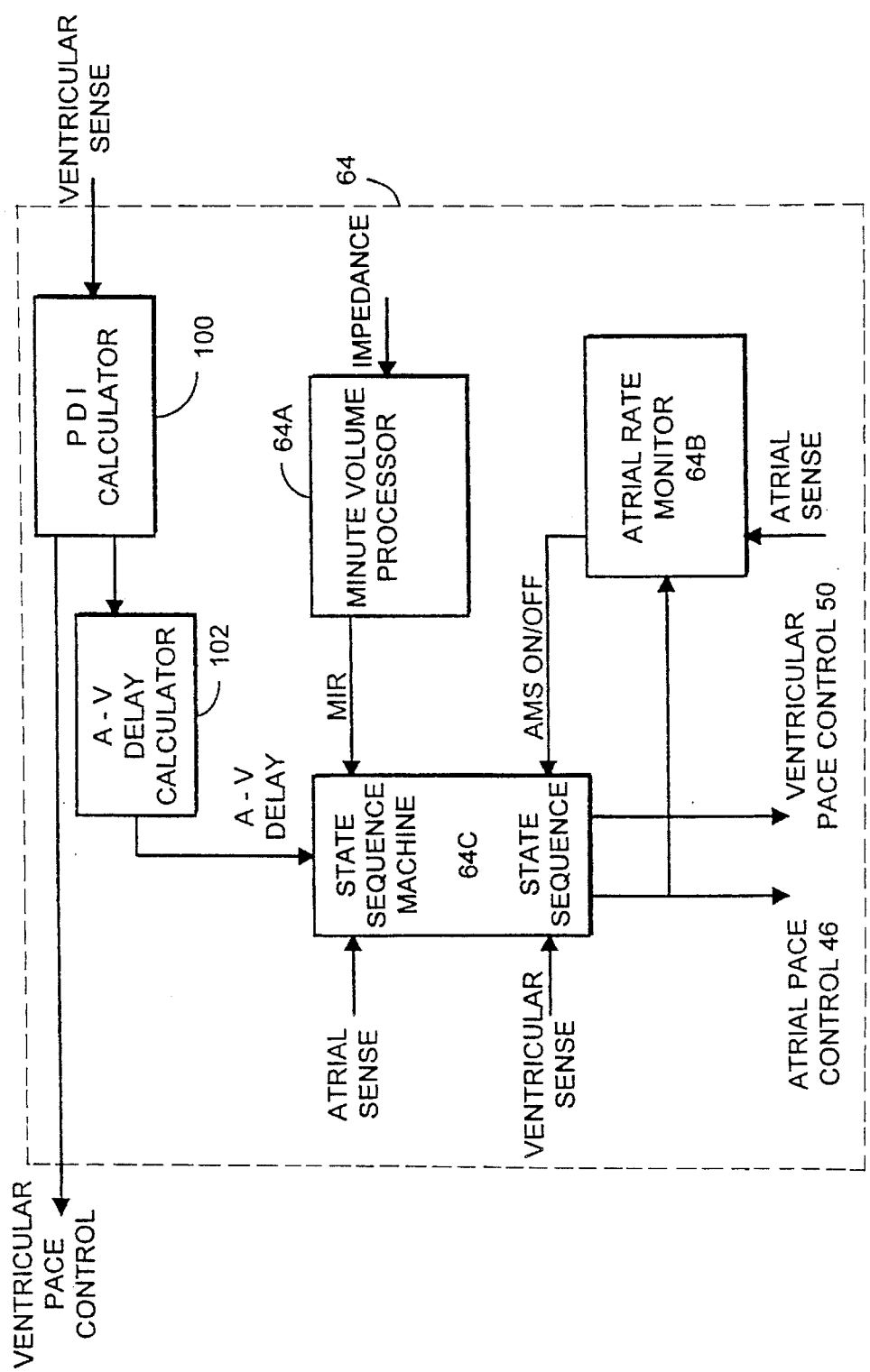
FIG. 4 shows details of the controller for the microprocessor of FIG. 3.

FIG. 4 shows the block diagram of the controller 64 of FIG. 3. The controller 64 includes a state sequence machine 64C, a minute volume processor 64A and an atrial rate monitor 64B. The minute volume processor 64A uses the data supplied via the internal bus 40 and the bus 22 from the impedance measurement block 42 to relate the minute volume indicated by the impedance measurement to the Metabolic Indicated Rate (MIR). This rate is then used by the machine 64C to vary the length of each interval in the timing cycle. While the pacemaker 10 is preferably operating in a DDD mode, it should be understood that it can operate in other modes as well. The atrial rate monitor 64B generates an Automatic Mode Switching (AMS) signal upon detection of a non-physiological atrial rate and rhythm. This AMS signal automatically switches the pacemaker 10 to a ventricular pacing mode, where atrial pacing is temporarily disabled. When a physiological atrial rate resumes, the AMS signal is deactivated and the pacemaker returns to an atrial tracking mode.

Importantly, in accordance with the present invention, controller 64 also includes a PDI calculator 100 and an A-V delay calculator 102. At the time the pacemaker is initialized, various parameters required for its automatic operation are either provided by the physician or set by the microprocessor as part of its initialization program. This initialization program includes the calculation of a base A-V delay which will result in an optimized cardiac output while the patient's heart is paced at a preselected rate. This calculation may be repeated and the A-V delay may be reset at regular intervals, for example, every 24 hours.

Over short periods of time if the pacing rate is changed the PDI also changes. In the normal sequence of events, increasing the pacing rate and keeping all other parameters constant should increase the value of PDI. This is, as explained before, due to the cardiac output staying the same but the stroke volume decreasing and hence the end-diastolic volume decreasing.

Figure 5:
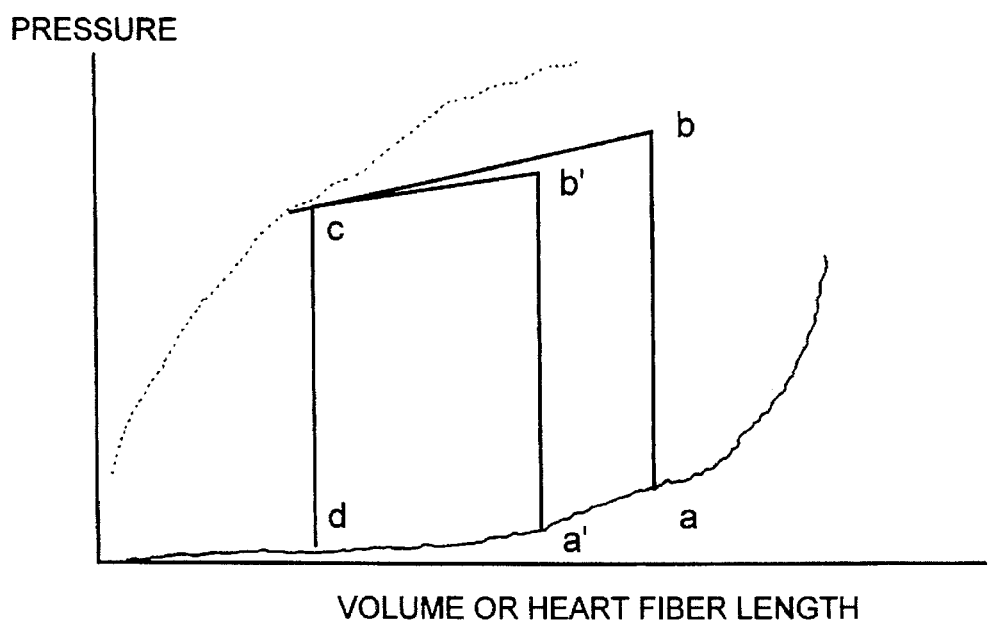
FIGS. 5, 5A and 5B shows typical variations of a heart (volume, or fiber length) as a function of pressure during a cardiac cycle.

The phenomenon discussed above is clearly illustrated in FIGS. 5, 5A and 5B. These figures show the relationship between pressure and volume (or muscle fiber length) of a heart during a typical cardiac cycle, assuming that at the systolic phase the volume remains constant independent of the heart rate. In this figure, the end of the systolic phase is shown by point d, the ventricle fills up, the ventricular volume increases towards point a. When the ventricle contracts, the pressure shoots up to point b. During the next phase, the ventricle is discharging from point b towards point c. By point d, the output ventricle valves have closed, the atrioventricular valves have opened and the whole cycle repeats. Importantly, at higher heart rates, the A-V delay is shorter so that the ventricle expands only to points a'-b' if cardiac output is to remain constant.

As the A-V delay lengthens and/or catecholamines increase the amount of ventricular relaxation along d-a, the PV loop shifts to the right and down, thus allowing an increase in cardiac output for an increase in metabolic demand.

Figure 5A:
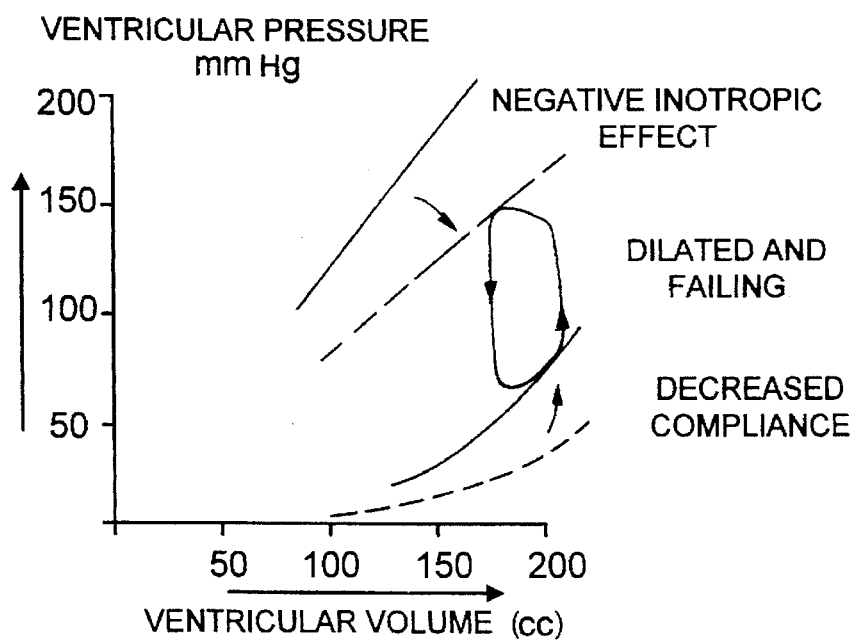

It is important to highlight two possible cardiac pathologies that may be ameriolated by the optimization of AV delay, with the use of PDI. FIG. 5A shows the PV loop for a failing heart. The objective here is to set the AV delay so as to shift the loop down and to the left.

Figure 5B:
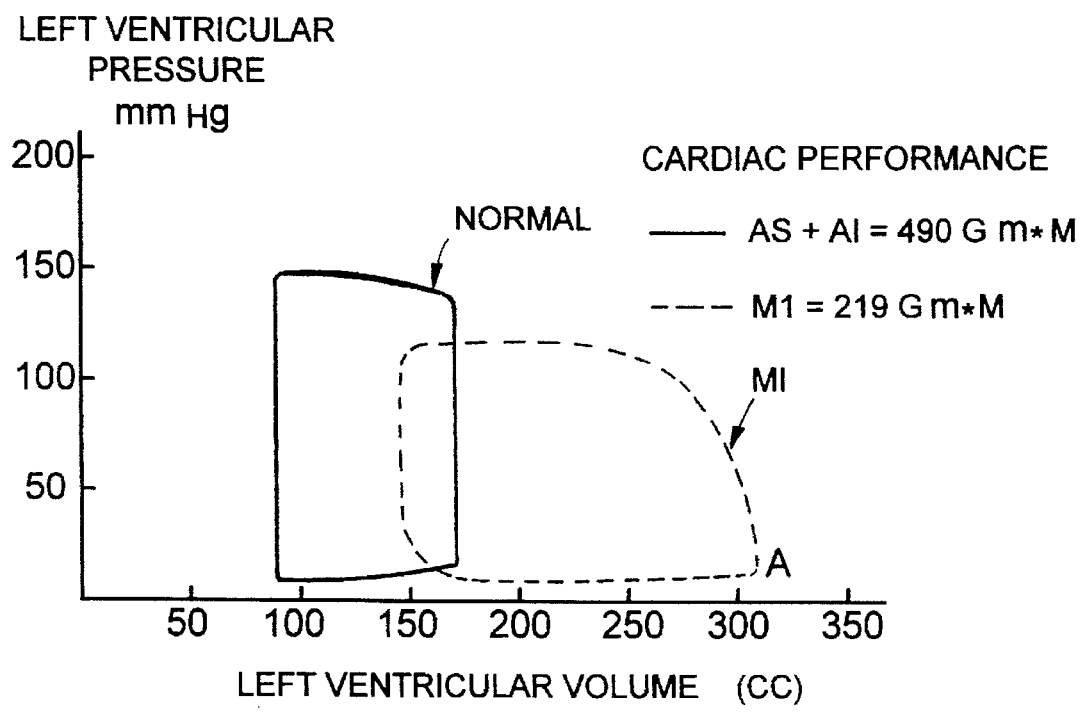

In FIG. 5B, a loop for mitral insufficiency (mitral regurgitation) is shown. Here it is desirable to wave point "A" in FIG. 5B as far left as possible, indicating minimum regurgitation.

To minimize regurgitation, the AV delay is adjusted so that, at any given pacing rate, the PDI is minimized. This minimized PDI reflects a maximized ventricular volume at the time of onset of its contraction and so, a minimization of mitral regurgitation. This, in turn, should help alleviate the increase in preload which is precipitated by mitral regurgitation, and so help prevent the insideous push on the ventricle in the direction of heart failure.

Figure 6:
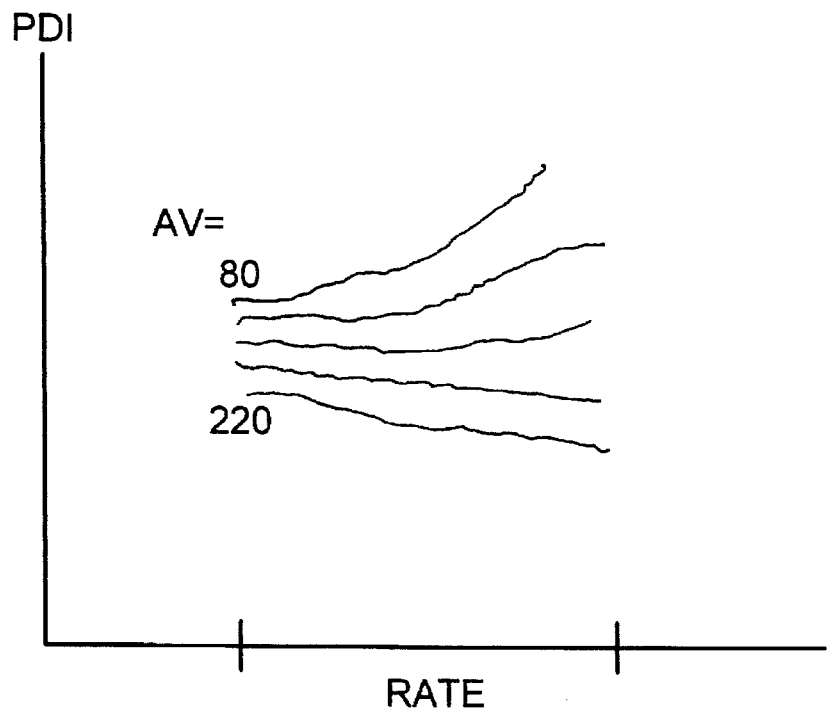
FIG. 6 shows variations of the PDI as a function of heart rate, at various A-V delays.

As indicated above, both the rate and the AV delay affect the end diastolic volume and consequently the PDI. FIG. 6 shows the relationship between PDI and heart rate at various delays ranging from 80 to 220 msec.

As the AV delay is shifted at a fixed rate, the PDI also changes. Ideally the PDI should be at a minimum in order to maximize the power of the stretched myocardium. However, a change in PDI must be used with rate to indicate that the rate is unloading the ventricle or at least not loading it even more as shown with a delay of 220 ms in FIG. 6. In medical terms, this process of optimization can be termed the maintenance of diastolic reserve.

Figure 7A:
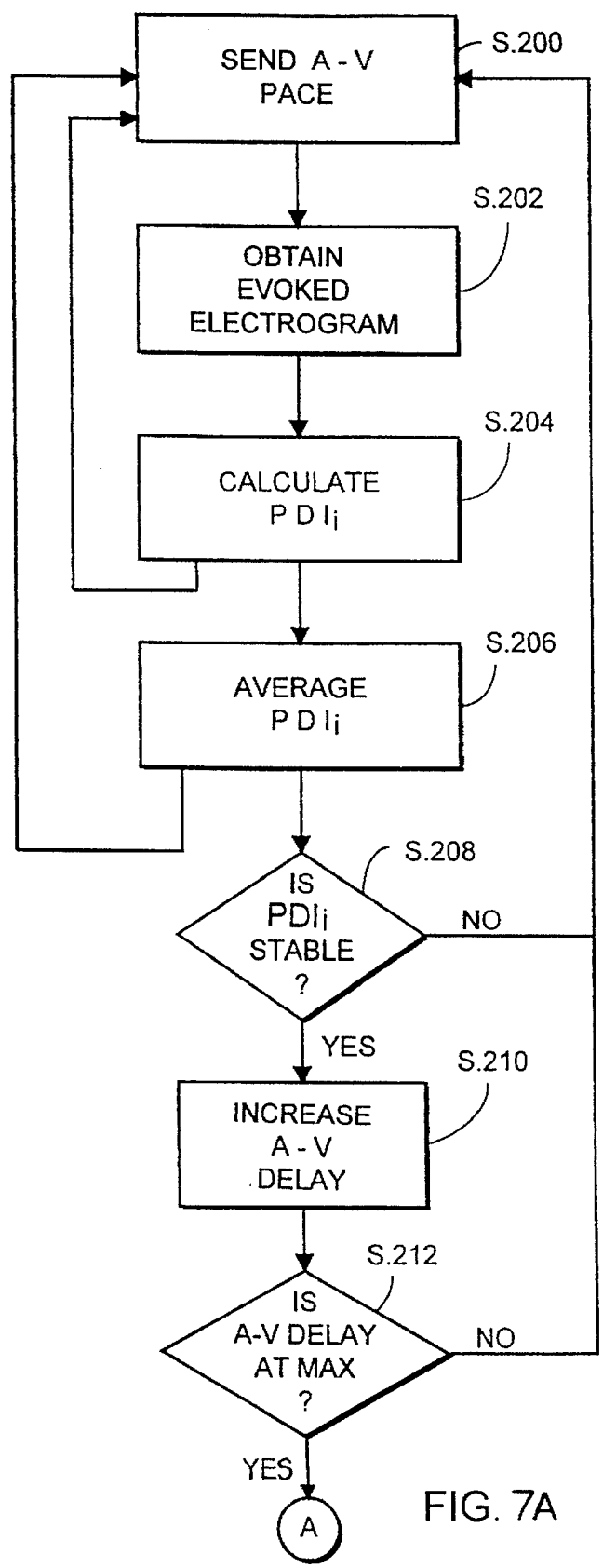
FIG. 7A and 7B show a flow chart for the controller of FIG. 4.
Figure 7B:
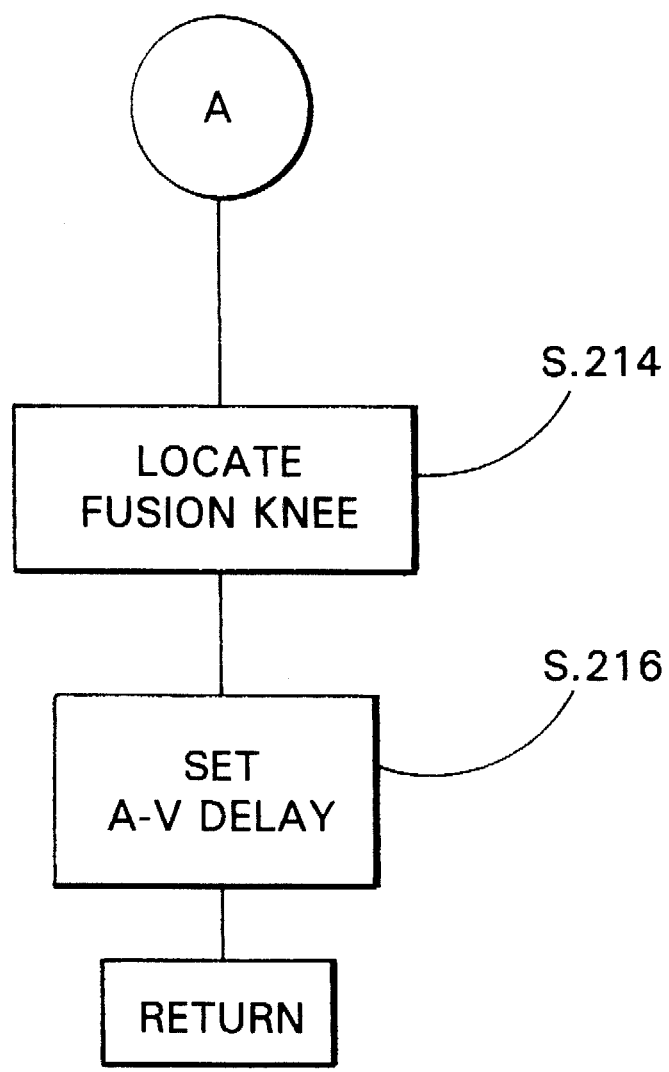
Figure 8:
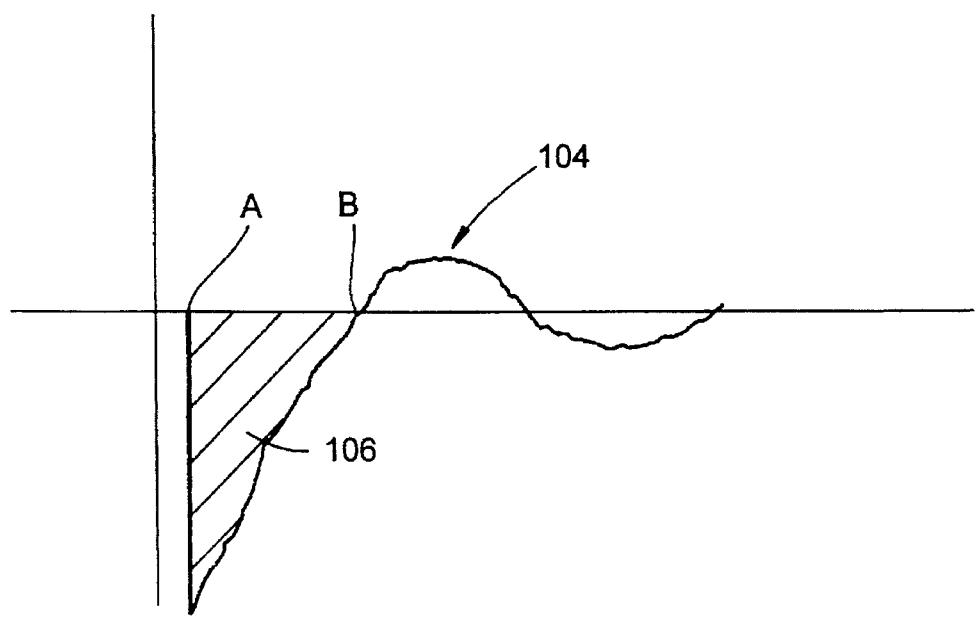
FIG. 8 shows a typical waveform used to determine the PDI parameter in the flow chart of FIGS. 7A and 7B.

Details of the operation of the PDI calculator 100 are shown in the flow chart of FIG. 7A and 7B. In step S200 an atrial (if necessary) and a ventricular pacing pulse are transmitted to the heart at a preset A-V delay of, for example, 40 ms. As mentioned above, the ventricular pulse is charge balanced. In step S202, the evoked electrogram corresponding to the pacing of step 200 is obtained from the ventricular cardiac lead 14. A typical evoked electrogram showing a QRST-complex waveform 104 is shown in FIG. 8.

Next, in step S204, the PDI parameter is calculated. As seen in FIG. 8, the PDI parameter is the area above curve 104 starting from the left at the point A where the curve 104 crosses the horizontal axis downward, until point B where the curve 104 crosses the horizontal axis again and becomes positive. This area is shaded as indicated by 106. The determination of parameter PDI is described in more detail in commonly assigned U.S. Pat. No. 5,184,615 to T. A. Nappholz, et al, which is incorporated herein by reference.

Steps 202–204 are performed several times in a row using the same A-V delay and pacing rate for a period covering a respiration cycle, i.e., about 3 seconds. The resulting measurements of $PDI_i$ are averaged as average $PDI_i$ in step 206. The whole sequence of steps 202–206 is repeated for another 3 second period to obtain another averaged PDI measurement and in step S208 the two averaged PDI measurements are compared to determine if the parameter is stable. For example, in step S208 the PDI parameter may be considered stable if the difference between two consecutive averaged $PDI_i$, $PDI_{i-1}$ is less than a certain preset value. If the difference is above the preset value, the results are discarded and the whole process is repeated. If the parameter is not stabilized within about 10–12 seconds, the process is suspended and run again at a later time.

The A-V Delay is gradually incriminated by 'Δ' which could be +10 ms. The maximum A-V delay is usually 280 ms.

Once the AV delay has been optimized the standby rate is incremented a specific amount, normally 20–30 ppm. The change in the PDI from the previous rate is computed. This is repeated over a respiratory cycle and the average change is computed. If the value is zero or positive the AV delay is maintained. If the PDI change is negative, the AV delay is then shortened until the PDI change for rate is zero. This process as discussed will ensure that the AV delay is optimized for most efficient operation, i.e., to give an increase in cardiac output for increased rate and not overload the heart more than necessary.

Once the AV delay is optimized at rest, only the rate increase versus PDI check is applied at higher rates. If the criteria for PDI change is not met AV delay will be shortened and the test repeated.

Figure 9:
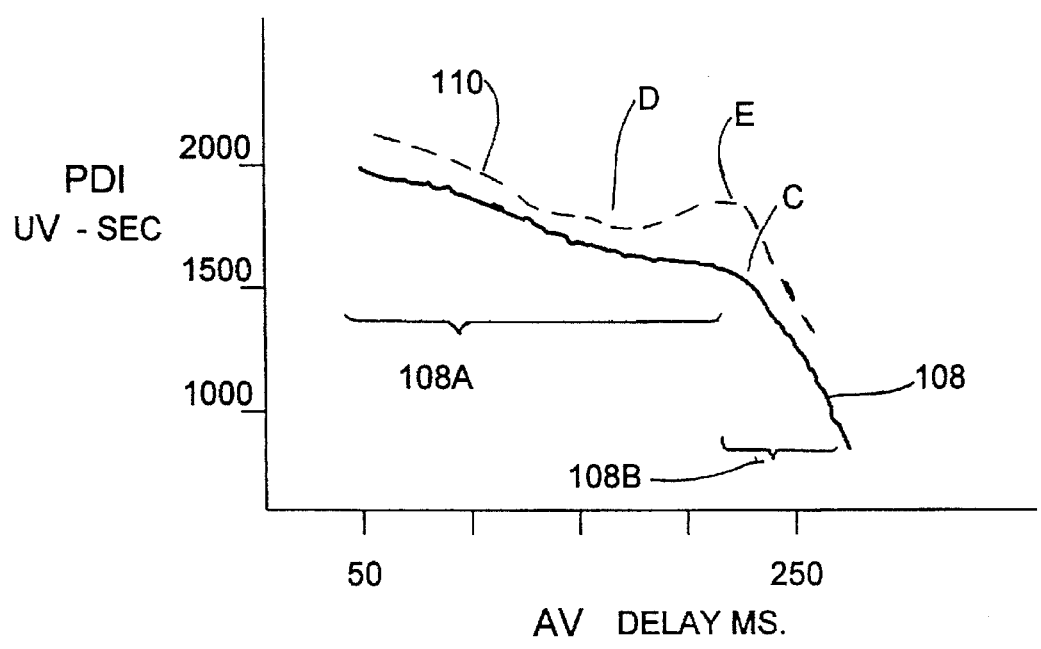
FIG. 9 shows a typical graph of the relationship between PDI and the A-V delay.

Curve 108 illustrating a typical relation between the PDI values and the corresponding A-V delay is shown in FIG. 9 at a particular pacing rate. As can be seen from this Figure, the curve 108 has two portions: The first portion, 108A, corresponds to the smaller A-V delay values and has a relatively low absolute slope. The second portion, 108B, corresponds to the larger A-V delay values, and has a larger absolute slope. The two portions are joined at knee point C. Portion 108B to the right of point C characterizes a region where the ventricle undergoes fusion beats. This term refers to a phenomenon wherein the ventricle is partially depolarized because of the natural conduction from the atrium to the ventricle. Because of the partial depolarization, the QRST wave is incomplete and hence the PDI value in the portion 108B is meaningless.

In step S214, the location of the knee point C indicative of the fusion knee is calculated. This step can be performed, for example, by taking points along the curve 108 and extrapolating the slopes between adjacent points. Another method of determining the fusion knee is by determining the natural A-V duration of the patient. The fusion knee point C then can be estimated to be slightly longer than this natural A-V duration. In case of blockage of the natural AV conduction, the default value for the position of the knee can be set to about 280 msec.

Next, in step S216, the optimum value of the A-V delay is selected. As previously mentioned, at a constant heart rate, cardiac output is inversely related to the PDI, whereby as the PDI decreases, the cardiac output increases. Therefore the A-V delay should be set to the minimum PDI value possible. However, as also mentioned above, beyond the knee point C, the PDI value has no practical meaning. Therefore the A-V delay is set in step S216 to a value which is slightly smaller (for example by about 10 msec) than the position of the fusion knee. The whole process may be repeated for a plurality of pacing rates thereby developing a family of curves similar to 108, each curve being specific to a pacing rate.

Some patients, such as the ones, for example, who are suffering from regurgitation into the atrium due to a defective atrioventricular valve, have a PDI curve which is different from the curve 108. More specifically, in such patients, the PDI and A-V delay are related by a curve 110 which has a low point D below the knee point E. For these patients, in step S216, the optimum A-V delay is set to correspond to this low point D disposed to the left of and rather than adjacent to the knee point E.

Referring back to FIG. 4, the PDI calculator generates the atrial and ventricular pacing signals and monitors the evoked electrogram to determine the corresponding PDI value. The PDI values thus collected are provided for the A-V delay calculator 102 which calculates or determines the optimum A-V delay for the patient as set forth above. This delay is provided to the sequence machine 64C which then proceeds to pace the heart accordingly.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. A pacemaker for regulating a patient's heart, comprising:

a measuring element for measuring an evoked depolarization potential indicative of the diastolic volume of blood in a chamber of the patient's heart;

a pacing parameter generator for generating a pacing parameter; and a pacing pulse generator for generating pacing pulses for said heart in accordance with said pacing parameter;

wherein said pacing parameter generator includes a selector for adjusting said pacing parameter to maximize a cardiac output indicated by said evoked depolarization potential at different pacing rates.

2. The pacemaker of claim 1 wherein said pacing parameter generator includes an A-V selector defining an A-V delay.

3. The pacemaker of claim 1 wherein said measuring element includes an evoked depolarization potential sensor for generating a evoked depolarization potential waveform characteristic of said heart, and an integrator for integrating said depolarization waveform to generate a DPI parameter.

4. The pacemaker of claim 3 wherein said volume parameter generator derives said volume parameter from an integral of said evoked depolarization potential waveform, said selector selecting said pacing parameter based on said DPI parameter.

5. The pacemaker of claim 4 wherein said pacing parameter generator includes an A-V selector defining an A-V delay.

6. A pacemaker for implantation in a patient's body for regulating the patient's heart, comprising:

a sensor for sensing cardiac signals generated in a chamber of the patient's heart, said cardiac signals including an evoked depolarization potential signal responsive to a pacing pulse;

a pulse generator for applying pacing pulses to said chamber;

a pacing parameter generator for generating a pacing parameter;

a timer for timing said pacing pulses in accordance with said pacing parameter; and a volume parameter generator for determining a volume parameter from said evoked depolarization potential signal, said volume parameter being indicative of a diastolic volume of blood pumped by said chamber; and said pacing parameter generator including a selector for selecting said pacing parameter in accordance with said volume parameter to maximize a cardiac output indicated by said volume parameter.

7. The pacemaker of claim 6 wherein selector generates a cardiogram based on said cardiac signals and volume parameter generator generates said volume parameter from said cardiogram.

8. The pacemaker of claim 7 wherein said cardiogram includes a QRST complex wave, and wherein said volume parameter generator includes a separator for separating a portion of said QRST complex wave and wherein volume parameter generator integrates said portion to generate said volume parameter.

9. The pacemaker of claim 6 wherein said pacing parameter generator includes an A-V selector defining an A-V delay.

10. The pacemaker of claim 6 wherein said pulsing means selectively generates atrial and ventricular pacing pulses.

11. The pacemaker of claim 6 wherein said volume parameter generator comprises an integrator for integrating said evoked depolarization potential to generate a DPI parameter and wherein said selector selects said pacing parameter based on said DPI parameter.

12. A method of regulating a patient's heart comprising the steps of:

generating pacing pulses for said cardiac chamber;

sensing cardiac signals from a cardiac chamber including evoked depolarization potential signals resulting from said pacing pulses;

generating a volume parameter indicative of a diastolic volume of blood being pumped by said chamber in response to said pacing pulses, said volume parameter being derived from said evoked depolarization potential signals; and generating a pacing parameter selected to optimize said volume of blood as indicated by said volume parameter at different rates, said pacing parameter defining a characteristic of said pacing pulses.

13. The method of claim 12 wherein said step of generating said volume parameter comprises performing a plurality of measurements sequentially during an initiation phase to obtain a plurality of volume parameter values, each volume parameter value corresponding to a pacing parameter value, and selecting the pacing parameter value which corresponds to a volume parameter value indicative of a maximum cardiac output.

14. The method of claim 12 wherein said step of measuring said volume parameter is performed by generating an electrogram from said cardiac signals.

15. The method of claim 14 wherein said step of measuring said volume parameter is further performed by identifying a portion of said electrogram and integrating said portion.

16. The method of claim 12 wherein said step of generating said pacing parameter includes defining an A-V delay.

17. The method of claim 16 further comprising the step of adjusting said pacing parameter after said initiation phase in accordance with a metabolic demand parameter.

* * * * *